United States Patent [19]
Matsui et al.

[11] 3,946,065
[45] Mar. 23, 1976

[54] PRODUCTION OF CYCLOPENTANE DERIVATIVES

[75] Inventors: Masanao Matsui, Tokyo; Junki Katsube, Tononaka; Hiromi Shimomura; Eichi Murayama, both of Takarazuka, all of Japan

[73] Assignee: Sumitomo Chemical Co., Ltd., Osaka, Japan

[22] Filed: Apr. 30, 1971

[21] Appl. No.: 139,239

[30] Foreign Application Priority Data

| | | |
|---|---|---|
| Apr. 30, 1970 | Japan | 45-37358 |
| Sept. 26, 1970 | Japan | 45-84293 |
| Sept. 26, 1970 | Japan | 45-84294 |
| Sept. 26, 2970 | Japan | 45-84295 |
| Sept. 25, 1970 | Japan | 45-84296 |
| Oct. 30, 1970 | Japan | 45-96302 |

[52] U.S. Cl....... 260/464; 260/239 AA; 260/465 D; 260/468 D; 260/514 D; 260/543 R; 260/546; 260/557 R
[51] Int. Cl.²............... C07C 120/00; C07C 121/46
[58] Field of Search....................... 260/464

[56] References Cited
UNITED STATES PATENTS

| | | | |
|---|---|---|---|
| 3,304,167 | 2/1967 | Buntin et al. | 260/464 X |
| 3,409,659 | 11/1968 | Pruett et al. | 260/464 |
| 3,432,541 | 3/1969 | Bagli et al. | 260/464 X |
| 3,470,248 | 9/1969 | Brotherton et al. | 260/464 X |
| 3,483,102 | 12/1969 | Arnold et al. | 260/464 X |
| 3,492,330 | 1/1970 | Trecker et al. | 260/464 X |
| 3,723,423 | 3/1973 | Andersen et al. | 260/464 X |
| 3,751,463 | 8/1973 | Caton et al. | 260/464 X |
| 3,832,380 | 8/1974 | Matsui et al. | 260/464 X |

OTHER PUBLICATIONS

Migrdichian, "Organic Synthesis," Vol. 1, 1957, pp. 330–331.

Wagner & Zook, "Synthetic Organic. Chemistry", 1953, pp. 169–170, 494.

*Primary Examiner*—Joseph P. Brust
*Attorney, Agent, or Firm*—Sughrue, Rothwell, Mion & Zinn

[57] ABSTRACT

Cyclopentane derivatives of the formula

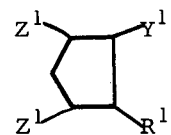

wherein $R^1$ is a group of the formula $$-(CH_2)_n-X$$

in which X is a carboxyl group or its homologue, a halogen atom or a hydroxyl group and $n$ is an integer of from 1 to 7; $Y^1$ is a formyl group of a carboxyl group or its homologue; and $Z^1$ is a formyl group, a carboxyl group, a hydroxymethyl group, an acetyl group, an acetoxy group, or a hydroxyl group and a process for their preparation are disclosed. The process schematically comprises the Diels-Alder reaction of a compound having the formula $R^1-CH=CH-Y^1$ with cyclopentadiene followed by oxidation of the bicycloheptene reaction product formed into a cyclopentane derivative in which $Z^1$ is a formyl group, a hydroxymethyl group or a carboxy group. Subsequent conversion of this cyclopentane derivative by methylation into a diacetyl cyclopentane compound followed by peroxidation and hydrolysis results in the production of a series of cyclopentane derivatives which are useful, for example, as intermediates for the production of prostaglandins.

15 Claims, No Drawings

PRODUCTION OF CYCLOPENTANE DERIVATIVES

BACKGROUND OF THE INVENTION

This invention relates to novel cyclopentane derivatives and a process for their production. More specifically, the invention pertains to novel cyclopentane derivatives of the formula

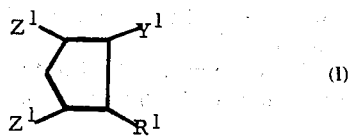

wherein $R^1$ is a group of the formula

in which X is a carboxyl group or its homologue, a halogen atom or a hydroxyl group and $n$ is an integer of from 1 to 7; $Y^1$ is a formyl group or a carboxyl group or its homologue; and $Z^1$ is a formyl group, a carboxyl group, a hydroxymethyl group, an acetyl group, an acetoxy group or a hydroxyl group.

The cyclopentane derivatives of the formula (I) are useful as intermediates for the production of medicines, for example, prostaglandins which have broad pharmacological action such as vassodepressors, stimulants of smooth muscle, gastric secretion inhibitors, reducers of platelet stickiness or inhibitors of thrombus formation and therefore attract great attention in medical and pharmacological fields.

Out extensive work has led to the discovery that such useful prostaglandins and their homologues can be obtained with great industrial advantage from the cyclopentane derivative of the formula (I).

Typical examples of processes for producing prostaglandins are schematically shown as follows:

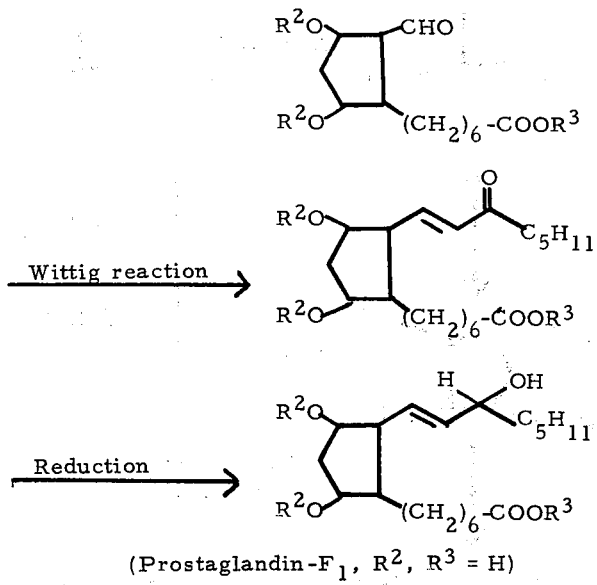

(Prostaglandin-$F_1$, $R^2$, $R^3$ = H)

Prostaglandin-$F_2$ also can be obtained from the cyclopentane derivative of the formula (I), wherein X is a halogen or a hydroxyl group, and $n$ is 2, or X is a carboxyl group or its homologue, and $n$ is 1, $Y^1$ is a formyl group or a carboxyl group or its homologue and $Z^1$ is an acetoxy group or a hydroxyl group.

The production of the prostaglandins described above is only an example of the application of the cyclopentane derivatives of the present invention, and it should be noted that the utilities of the cyclopentane derivatives of the invention are not limited to it.

An object of the present invention is to provide novel cyclopentane derivatives which are useful as intermediates for the preparation of medicines.

Another object of the present invention is to provide a process for producing these novel cyclopentane derivatives.

Other objects and advantages of the present invention will be apparent from the following description.

SUMMARY OF THE INVENTION

According to the present invention, the novel cyclopentane derivatives of the formula (I) above are produced by a process which comprises oxidizing a bicycloheptene derivative of the formula (II)

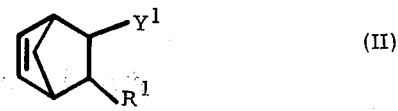

wherein $R^1$ and $Y^1$ are as defined above, to yield a cyclopentane derivative of the formula (Ia)

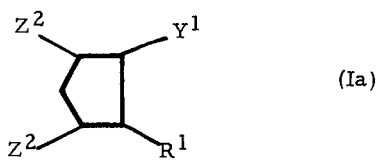

wherein $R^1$ and $Y^1$ are as defined above and $Z^2$ is a formyl group, a carboxyl group or a hydroxymethyl group, and, if desired, further oxidizing the cyclopentane derivative of the formula (Ia) in which $Z^2$ is a hydroxymethyl group, namely a cyclopentane derivative of the formula (Ib)

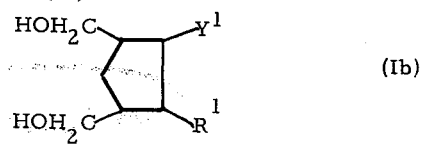

wherein $R^1$ and $Y^1$ are as defined above, to yield a cyclopentane derivative of the formula (Ia) in which $Z^2$ is a formyl group, namely a cyclopentane derivative of the formula (Ic)

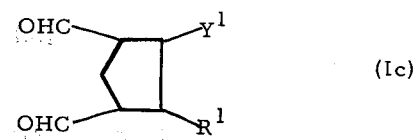

wherein $R^1$ and $Y^1$ are as defined above, and, if desired, further oxidizing the cyclopentane derivative of the formula (Ib) or (Ic), to yield a cyclopentane derivative of the formula (Ia) in which $Z^2$ is a carboxyl group, namely a cyclopentane-1,3-dicarboxylic acid derivative of the formula (Id)

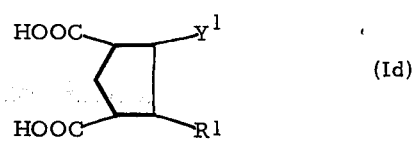

wherein $R^1$ and $Y^1$ are as defined above, and, if desired, converting the cyclopentane derivative of the formula (Ic) or (Id) to a diacetyl-cyclopentane derivative of the formula (Ie)

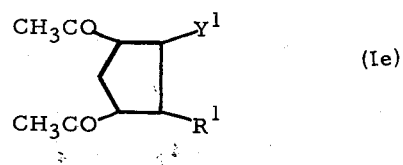

wherein R¹ and Y¹ are as defined above, and, if desired, reacting the diacetyl-cyclopentane derivative of the formula (Ie) with a peroxide, followed, if desired, by hydrolysis, to yield a cyclopentane-1,3-diol derivative of the formula (If)

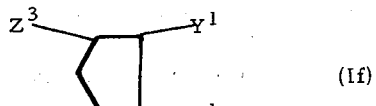

wherein R¹ and Y¹ are as defined above and Z³ is an acetoxy prior to hydrolysis or a hydroxyl group after hydrolysis.

The bicycloheptene derivative of the formula (II) is produced according to the invention by a Diels-Alder reaction of a compound of the formula (III)

$$R^1-CH=CH-Y^1 \qquad (III)$$

wherein R¹ and Y¹ are as defined above, with cyclopentadiene.

The reactions involved in the present invention are schematically illustrated as follows:

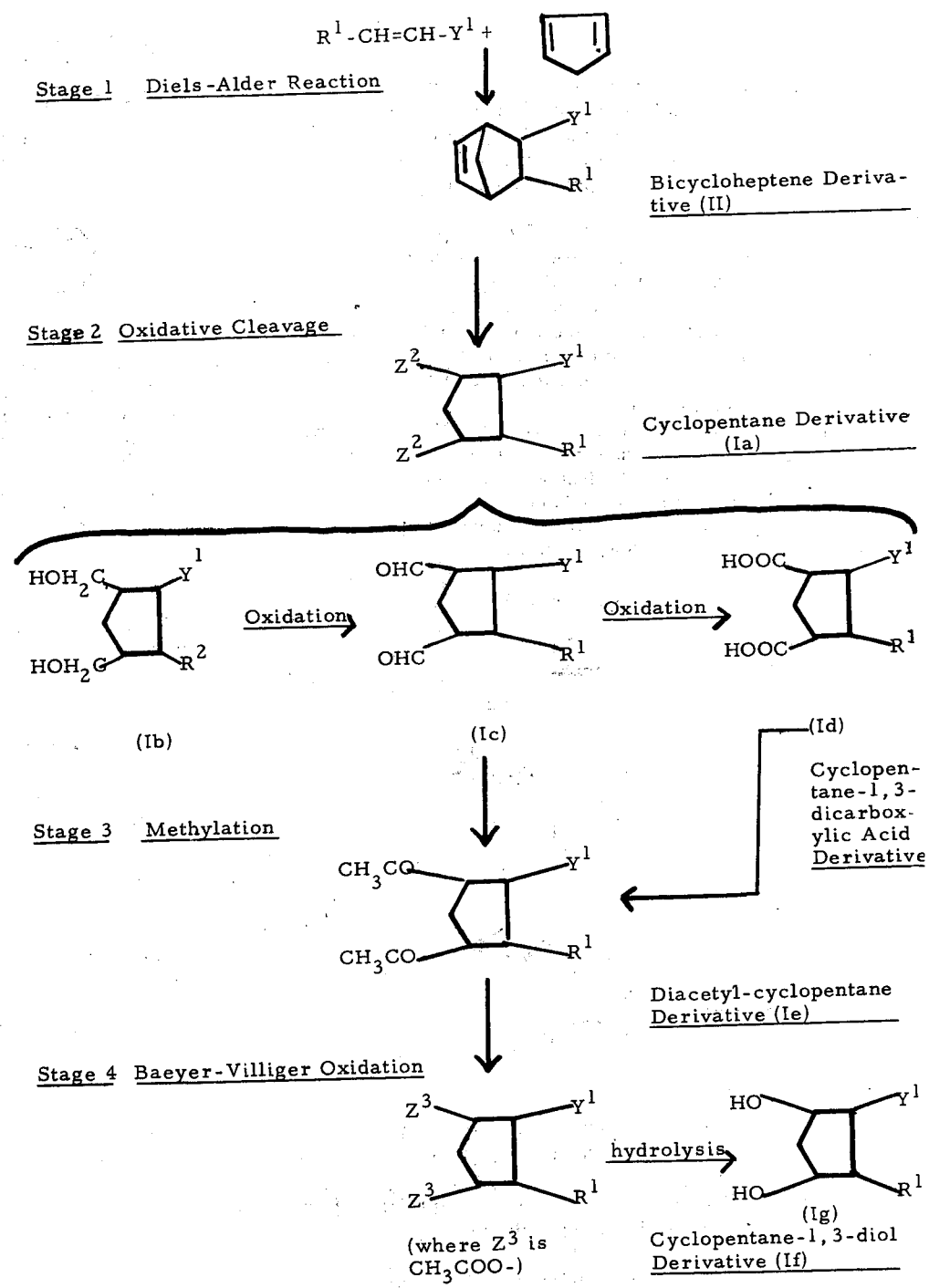

The term "homologue" of a carboxyl group as used throughout the specification and claims is intended to mean a group capable of being readily derived into a carboxyl group or derived from a carboxyl group by known methods. Examples of such include $C_1$–$C_4$ alkoxycarbonyl groups, such as methoxycarbonyl, ethoxycarbonyl and t-butoxycarbonyl, amide groups such as carbamoyl, methylcarbamoyl and dimethylcarbamoyl, or a cyano group and it may take any desired form within the scope of the definition depending upon the reaction conditions, after-treatment and the like. The formyl group represented by $Y^1$ may be converted, if desired, to a carboxyl group or its homologue at any stage by a known oxidative method, for example, the formyl group can be converted to a carboxyl group by treatment with oxidizing agents, such as potassium permanganate, chromium trioxide, sodium dichromate, silver oxide, peracid and the like, and the formyl group can be converted to a cyano group by oxination and subsequent dehydration.

On the other hand, the carboxyl group or its homologue may be converted, if desired, to a formyl group at any stage by known reductive methods, for example, the formyl group can be obtained from a carboxyl group by a Rosemund reaction, and from a cyano group by Stephen reaction or reduction with metal hydride compounds.

The formyl group represented by $Y^1$ is, however, rather sensitive toward the reactions involved in the present invention, and therefore during the course of the reactions of the invention it is preferable to protect the formyl group in a usual manner such as acetallization, or to generate the formyl group from the carboxyl group or its homologue at a later stage of the present invention.

Preferred examples of groups represented by $R^1$ include 1-substituted-methyl, 2-substituted ethyl, 5-substituted-pentyl, 6-substituted-hexyl and 7-substituted-heptyl.

DETAILED DESCRIPTION OF THE INVENTION

The process of the present invention will now be described below stage by stage.

STAGE 1

Production of Novel Bicycloheptene Derivatives of the Formula (III)

The bicycloheptene derivatives of the formula (II)

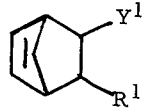

prepared in this stage are novel compounds except the case in which $R^1$ is a halomethyl group, and are obtained by reacting the compounds of the formula (III)

$$R^1-CH=CH-Y^1 \qquad (III)$$

with cyclopentadiene to form diene-adducts using the Diels-Alder reaction.

The compound of the formula (III) and cyclopentadiene may be directly mixed with each other to perform the reaction, but it is also possible to react them in an inert solvent, such as ether, benzene, toluene, xylene, methanol, ethanol, propanol, acetic acid or methylene chloride.

The reaction temperature is optional and can range from 0° to 200°C, but generally it is better to promote the reaction by heating. The ratio of the compound of the formula (III) to cyclopentadiene used in the reaction is optional and can range from 10:1 to 1:10.

The bicycloheptene derivative so obtained may be separated and purified by conventional methods such as chromatography and distillation.

The bicycloheptene derivative is considered to include four stereoisomers (diastreomers). This stereoisomerism is strongly restricted by the type of geometrical isomerism (trans and cis) of the starting compound of the formula (III). The stereosiomers may, if desired, be separated by known means, such as column chromatography as gas chromatography.

Most of the starting compounds of the formula (III) are novel compounds which are synthesized by the inventors of the present invention using several procedures; some examples of them are illustrated as follows:

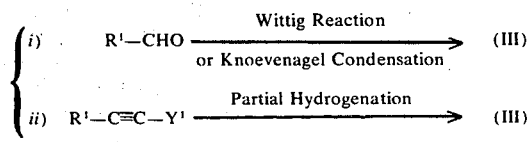

STAGE 2

Production of Novel Cyclopentane Derivatives of the Formula (Ia)

The novel cyclopentane derivatives of the formula (Ia)

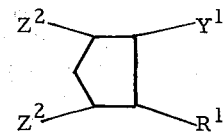

are produced by oxidizing the bicycloheptene derivatives of the formula (II), obtained in Stage 1, with ozone or other oxidizing agents to cleave the double bond.

The practice of the above-described process includes various embodiments. The group $Z^2$ of the product in this stage describes a functional group selected from the group consisting of a carboxyl group, a formyl group and a hydroxymethyl group depending upon the oxidation stage and the method of after-treatment.

Where the oxidation is carried out using ozone, this has to do with the after-treatment of ozonide which is a primary product.

When the after-treatment is hydrolysis or thermal decomposition, the group $Z^2$ of the product is a formyl group or a carboxyl group, and if if is oxidative decomposition, $Z^2$ of the product will be a carboxyl group. Reductive decomposition, on the other hand, gives a product in which $Z^2$ is formyl or hydroxymethyl.

The hydroxymethyl compound (Ib) may, if desired, be converted by conventional oxidative methods to the formyl compound (Ic), and moreover, the hydroxymethyl compound (Ib) or the formyl compound (Ic) may, if desired, be oxidized by conventional methods to the carboxyl compound (Id). The formyl compound (Ic) and the carboxyl compound (Id) are the starting materials of Stage 3 to be described.

The formation of the ozonide, which is the first stage of the oxidation with ozone, can be effected by contacting the bicycloheptene derivative of the formula (II) obtained in Stage 1 with ozone, preferably in an inert solvent. Any solvents generally used in ozone oxidations may be used. Suitable examples include petroleum ether, hexane, heptane, cyclohexane, ligroin, nitromethane, benzene, toluene, chloroform, methylene chloride, carbon tetrachloride, methanol, ethanol, isopropanol, acetic acid, methyl acetate, and ethyl acetate.

The reaction temperature used is optional and can range from −78°C to 100°C, but generally room temperature or lower temperatures are employed.

The ozone can be used in the stoichiometrical amount. Generally, it is advantageous to bubble ozone through the reaction system until the starting compound disappears.

The decomposition of the resulting ozonide may be performed by heating it directly, or putting it into water or an inert solvent heated to the desired temperature and generally a temperature over 100°C is preferable.

Typical examples of oxidative decomposition include the treatment of the ozonide with an oxidizing agent such as a manganese compound, a chromium compound or nitric acid, or the treatment of the ozonide with a mixture of hydrogen peroxide and an organic acid such as acetic acid or formic acid or with hydrogen peroxide alone, and the ratio of the oxidizing agents to the ozonide used in the reaction is optional and can range from 1:1 to 1:20 and the temperature employed in the reaction can vary depending on the kind of oxidizing agent, but generally the oxidation decomposition can be carried out at a temperature below 100°C.

Typical examples of reductive decomposition include the treatment of the ozonide with sulfur dioxide or a sulfite, the treatment of the ozonide with zinc powder and acetic acid, catalytic reduction of the ozonide using platnium-, palladium-catalysts and the like, or the treatment of the ozonide with a metal hydride compound such as lithium aluminum-hydride or sodium borohydride, and the reaction conditions employed in the reductive decomposition vary depending on the kind of reducing agent, but the ratio of reducing agent is generally used in an excess mole ratio to the ozonide, but in case a powerful reducing agent such as lithium aluminum hydride is used, a ratio near the stoichiometrical amount is preferable. The reaction temperature employed in the reaction varies depending on the kind of reducing agent, but in case a catalytic reduction or a reduction with a metal hydride compound is employed, the reaction can be carried out preferably at a temperature below room temperature.

On the other hand, the oxidative cleavage of the bicycloheptene derivative of the formula (II) to the cyclopentane derivative of the formula (Ic) or to the cyclopentane derivative of the formula (Id) can also be achieved by reacting the bicycloheptene derivative (II) with oxidizing agents other than ozone.

Although the practice of the above-described oxidation includes various embodiments, the variation mainly depends upon the type of the oxidizing agent employed in the reaction.

The bicycloheptene derivative (II) can be oxidized to the cyclopentane skeleton without isolating any intermediate by using fairly powerful oxidizing agents such as potassium permanganate, and the ratio of the oxidizing agent to the bicycloheptene derivative (II) or the reaction temperature employed in the reaction is optional, but generally a stoichiometric amount of the oxidizing agent is used at a temperature below room temperature.

Additionally, it is possible to cleave the double bond of the bicycloheptene derivative (II) in two steps. That is, the double bond is first oxidized to a vicinal glycol, and then the glycol is subjected to further oxidation to cleave the C—C bond. For the oxidation of the bicycloheptene derivative (II) to a vicinal glycol type intermediate, such agents as osmium tetraoxide or peracid are available, and for the oxidation of the vicinal glycol type intermediate to the cyclopentane derivative of the formula (Ia), such agents as periodic acid and its metal salts, lead tetraacetate, a manganese compound, a chromium compound are available. It should be noted that a combination agent such as osmium tetraoxide-sodium periodate or potassium permanganate-sodium periodate are also available for oxidation of the bicycloheptene derivative (II) to the cyclopentane derivative (Ia).

The type of the final product of the above-described oxidation depends on the type of oxidizing agent or the oxidizing conditions.

The resulting cyclopentane derivatives may be separated and purified by general procedures such as extraction, distillation or chromatography.

This product of Stage 2 could include eight stereoisomers (diastereoisomers) based on the four asymmetric carbon atoms. According to the reaction route of this stage, the two $Z^2$ groups assume a cis-configuration, and the configuration of $R^1$ and $Y^1$ is restricted by the configuration of the starting compound of the formula (II). Accordingly, the process of this stage has the advantage that the intended product can be synthesized stereo-selectively by properly choosing the starting compound.

STAGE 3

Production of Novel Diacetyl-Cyclopentane Derivatives of the Formula (Ie)

The novel diacetyl-cyclopentane derivatives of the formula (Ie)

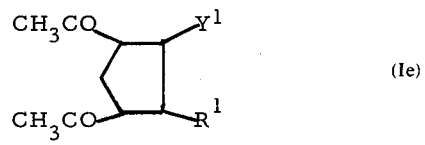

(Ie)

are produced by methylation of active carboxylic acid derivatives of the cyclopentane-1,3-dicarboxylic acid derivatives of the formula (Id) obtained in Stage 2

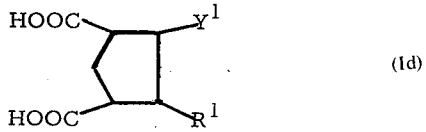

(Id)

or by methylation of the cyclopentane derivative of the formula (Ic) obtained in Stage 2.

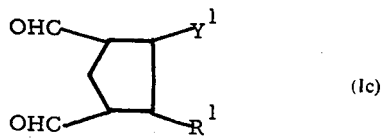

i. The procedure from the active carboxylic acid derivatives of the cyclopentane-1,3-dicarboxylic acid derivatives (Id) to the diacetylcyclopentane derivatives (Ie) is as follows.

First of all, the novel diacetyl-cyclopentane derivatives (Ie) are produced by reacting the active carboxylic acid derivatives of the cyclopentane-1,3-dicarboxylic acid derivatives (Id) with a metal methyl compound.

Alternatively, these compounds of the formula (Ie) are produced by reacting the active carboxylic acid derivatives of the cyclopentane-1,3-dicarboxylic acid derivatives (Id) with diazomethane to form novel bis-diazoacetylcyclopentane derivatives of the formula (Id')

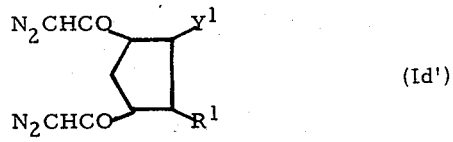

or contacting the resulting bis-diazoacetyl-cyclopentane derivatives of the formula (Id') with a hydrogen halide such as hydrogen chloride or hydrogen bromide to form novel bis-haloacetyl-cyclopentane derivatives of the formula (Id'')

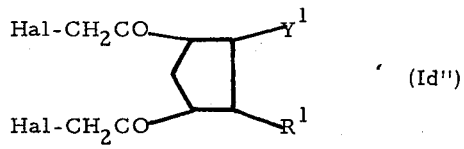

wherein Hal is halogen, and subjecting the diazoacetyl group of the compound (Id') or the haloacetyl group of the compound (Id'') to a reductive hydrogen substitution reaction.

The active carboxylic acid derivatives described above are intended to cover ordinary carboxylic acid derivatives capable of readily reacting with a metal methyl compound or diazomethane, and their examples are acid halides, mixed acid anhydrides, and active esters such as p-nitrophenyl esters, pentachlorophenyl esters.

The process for producing these active carboxylic acid derivatives will be explained as follows. The acid halides of the cyclopentane-1,3-dicarboxylic acid derivatives of the formula (Id) may be prepared by general methods of converting carboxylic acids to acid halides. Specifically, this is accomplished, for example, by a method of reacting the cyclopentane-1,3-dicarboxylic acid derivatives of the formula (Id) with thionyl chloride, thionyl bromide, phosphorus trichloride, phosphorus tribromide, or phosphorus pentachloride, a method of reacting them with oxalic chloride or oxalic bromide by heating, or reacting them with phosgene using dimethyl formamide as a catalyst.

The preparation of the mixed acid anhydride is accomplished by condensing the cyclopentane-1,3-dicarboxylic acid derivatives of the Formula (Id) with a halocarbonic acid alkyl ester such as methyl chlorocarbonate or ethyl chlorocarbonate in the presence of a base. The base is used in an amount capable of supplementing a halic acid formed by the condensation reaction. Typical examples of the base used in this reaction include organic tertiary bases such as triethyl amine, or dimethyl aniline, alkali hydroxides such as sodium hydroxide and potassium hydroxide, and alkali alkoxides such as sodium ethylate or sodium methylate.

Advantageously, this reaction is performed in an inert solvent such as ether, tetrahydrofuran, dioxane, dimethoxyethane, diethylene glycol dimethyl ether, benzene, toluene, or methylene chloride.

The reaction of such an active carboxylic acid derivative with a metal methyl compound is performed by contacting them in an inert solvent.

Typical examples of the metal methyl compound include Grignard reagents such as methyl magnesium iodide or methyl magnesium bromide, methyl lithium, methyl cadmium, and methyl zinc. Methyl cadmium and methyl zinc are especially noted because they act strongly on the active carboxyl group but hardly on the other functional groups.

Generally, it is advantageous to use the metal methyl compound in about a stoichiometrical amount. The reaction temperature employed in the reaction is optional and can range from −20° to 100°C. As the inert solvent, solvents such as ether, dioxane, dimethoxyethane, diethylene glycol dimethyl ether, benzene or toluene are used. The reaction temperature may be chosen within the range below the boiling point of the solvent used.

In an alternative embodiment of the present procedure, the active dicarboxylic acid derivatives are reacted with diazomethane to convert them to a diazoketone structure (Id').

The reaction is performed by contacting them with diazomethane in an inert solvent such as ether, dimethoxyethane, heptane, hexane, benzene or toluene.

The resulting bis-diazoacetyl-cyclopentane derivatives of the formula (Id') having the diazoketone structure may be readily converted to bis-haloacetyl-cyclopentane derivatives of the formula (Id'') having a haloketone structure by contacting with a hydrogen halide such as hydrogen chloride or hydrogen bromide.

Where the acid halide derivative of the cyclopentane-1,3-dicarboxylic acid derivative of the formula (Id) is reacted with diazomethane to yield the bis-diazoacetyl-cyclopentane derivative of the formula (Id'), if the amount of diazomethane is small, hydrogen halide formed by the reaction acts on the bis-diazoacetyl-cyclopentane derivative of the formula (Id') and converts it to the bis-haloacetyl-cyclopentane derivative (Id"). Hence, when it is desired to obtain the bis-diazoacetyl-cyclopentane derivative of the formula (Id') advantageously, it is better to use diazomethane in an excess amount (several times the stoichiometric amount) so as to consume the free hydrogen halide.

On the other hand, when the production of the bis-haloacetyl-cyclopentane derivative is intended, it is preferred that diazomethane be used in an amount equimolar to, or less than, the acid halide derivative. It is more advantageous, however, to form the bis-diazoacetyl-cyclopentane derivative of the formula (Id') first, and then contact it with a hydrogen halide of greater than the corresponding amount (several times) to form the bis-haloacetyl-cyclopentane derivative (Id").

The bis-diazoacetyl-cyclopentane derivative (Id') or bis-haloacetyl-cyclopentane derivative (Id") is then reductively converted to the diacetyl-cyclopentane derivative of the formula (Ie).

One effective reducing method for the bis-diazoacetyl-cyclopentane derivative of the formula (Id') involves contacting it with an aqueous solution of hydroiodic acid as follows:

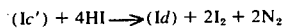

The reaction is performed by contacting the bis-diazoacetyl-cyclopentane derivative of the formula (Id') with at least 4 times on a molar basis the amount of an aqueous solution of hydroiodic acid at a temperature substantially below room temperature either directly or in an inert solvent such as ether, chloroform, carbon tetrachloride, methylene chloride or benzene.

On the other hand, the reduction of the bis-haloacetyl-cyclopentane derivative of the formula (Id") is carried out especially by using zinc or by the catalytic reducing method. Zinc is used in a powder form together with water, alcohol, acid or alkali. An especially effective method comprises reacting the bis-haloacetyl-cyclopentane derivative (Id") with zinc powder in an organic acid such as acetic acid or a mineral acid such as hydrochloric acid. The catalytic reduction is accomplished by contacting the bis-haloacetyl-cyclopentane derivative (Id") with molecular hydrogen in the presence of a catalyst such as palladium, and the reaction generally proceeds at a temperature below room temperature.

ii. An alternative procedure for this stage is a conversion from the cyclopentane derivatives of the formula (Ic) to the diacetyl-cyclopentane derivatives of the formula (Ie). This process can be accomplished by contacting the cyclopentane derivatives of the formula (Ic) with diazomethane in an inert solvent such as ether, dimethoxyethane, dioxane, benzene, ethyl acetate, chloroform and the like. The reaction temperature employed in this procedure is substantially below room temperature and the reaction time is optional and can range from 0.5 hour to 48 hours.

The final product of this stage, diacetyl-cyclopentane derivative of the formula (Ie) is generally obtained as an oily substance. If desired, it may be refined using conventional methods.

The products of the formula (Ie) could include eight stereoisomers (diastereoisomers). However, the stereoisomerism is restricted by the steric configuration of the starting compound, the cyclopentane-1,3-dicarboxylic acid derivative.

The process of Stage 3 can be practiced irrespective of the stereoisomerism, and therefore, is applicable to a mixture of stereoisomers, and if desired, to compounds having specific steric configurations.

STAGE 4

Production of Novel Cyclopentane-1,3-diol of the Formula (If)

The novel cyclopentane-1,3-diol derivatives of the formula (If)

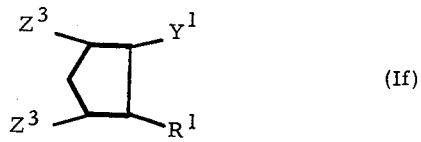

are prepared by reacting the novel diacetylcyclopentane derivatives of the formula (Ie) obtained in Stage 3

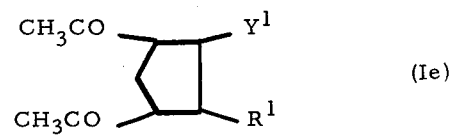

with peroxides, followed, if desired, by hydrolysis. The group $Z^3$ of the product of this stage is an acetoxy group prior to hydrolysis and a hydroxyl group after hydrolysis.

The process of this stage can be carried out under various conditions, but basically by reacting the starting compound of the formula (Ie) with a peroxide in an inert solvent on the basis of Baeyer-Villiger reaction.

Examples of peroxides which can be used in this reaction include organic peroxides such as peracetic acid, performic acid, perbenzoic acid, meta-chloroperbenzoic acid, perphthalic acid, permaleic acid or trifluoroperacetic acid, persulfuric acid, and hydrogen peroxide.

As the inert solvent such compounds as acetic acid, chloroform, methylene chloride, ether, hexane, benzene, carbon tetrachloride, and ethyl acetate are used.

The reaction temperature and time can be optionally determined on consideration of the correlation between them, but the reaction temperature may be any temperature below the boiling point of the solvent used. The mole ratio of the peroxide to the diacetyl-cyclopentane derivative (Ie) is optional, but it is advantageous to use the peroxide in an excess amount to the diacetylcyclopentane derivative (in the range of several times to 20 times).

The reaction may, if desired, be promoted by adding a strong acid such as perchloric acid, sulfuric acid, or toluenesulfonic acid.

The final product of the formula (If) is generally obtained as an oily substance, which can be purified by methods known in the art, such as chromatography. The product may be separated after hydrolyzing its acetoxy group to a hydroxyl group.

The diacetoxy compound obtained by the aforedescribed reaction with the peroxide may be converted to a diol derivative (Ig) by hydrolysis. The diol derivative may be obtained by hydrolyzing the product at the same time as its separation or after separation. Conventional ester hydrolysis conditions are employed.

The product of the formula (If) could have a number of stereoisomers (diastereomers). The process of this stage, however, is applicable to a mixture of stereoisomers, and if desired, to compounds having specific steric configurations.

The present invention will be described further by reference to the following Examples which are presented for illustrative, rather than limitative, purposes.

Examples 1 to 12 relate to Stage 1, Examples 13 to 23 to Stage 2, Examples 24 to 31 to Stage 3, and Examples 32 to 35 to Stage 4.

EXAMPLE 1

3.0 grams of 9-carboethoxy-2-trans-nonenal and 10 g of cyclopentadiene were diluted with 5 ml of toluene, and the solution was heated in an autoclave for 7 hours at about 120°C.

The product was treated in an usual manner. The crude oily substance obtained was subjected to chromatograhy on silica gel to yield 0.5 g of bicyclo[2.2.1]hept-5-ene-3-endo-(6'-carboethoxyhexyl)-2-exocarboxaldehyde and 0.4 g of bicyclo[2.2.1]hept-5-ene-3exo-(6'-carboethoxyhexyl)-2-endo-carboxaldehyde. There was recovered 1.8 g of unreacted nonenal derivative.

The bicycloheptene derivatives were obtained as oily substances and had the following characteristics:

2-exo-carboxaldehyde derivative: Infrared absorption (film method, unit $cm^{-1}$): 2820, 2720, 1735, 1720, 1240, 1170; nuclear magnetic resonance [60 Mc, unit ppm from tetramethylsilane (TMS) (in $CCl_4$)]; the aldehyde proton appeared at 9.7 as doublet (coupling constant J=2 cps).

2-endo-carboxyaldehyde derivative. Infrared absorption (film method, unit $cm^{-1}$): 2820, 2720, 1735, 1720, 1240, 1170; nuclear magnetic resonance (in $CCl_4$, unit δ value, ppm from TMS): the aldehyde proton appeared at 9.3 as doublet (J=3 cps).

EXAMPLE 2

2.1 grams of 9-carboethoxy-2-cis-nonenal and 1.4 g of cyclopentadiene were diluted with 15 ml of toluene, and the solution was heated in an autoclave for 4 hours at about 130°C.

The product was subjected to chromatography on silica-gel to yield oily bicyclo[2.2.1]hept-5-ene-3-(6'-carboethoxyhexyl)-2-carboxaldehyde. There was recovered 1.3 g of unreacted nonenal derivative.

The properties of this bicycloheptene derivative were as follows. Infrared absorption (film method): 2820, 2720, 1735, 1720, 1240, 1170.

EXAMPLE 3

The bicycloheptene(2-exo-carboxaldehyde) derivative obtained in Example 1 was dissolved in a cold aqueous solution of sodium hydroxide to saponify the ester group on the side chain, and precipitated with an acid to separate it as the free acid, followed by purification. There was obtained bicyclo-[2.2.1]hept-5-ene-3-(6'-carboxyhexyl)2-carboxyaldehyde. Its main component was an aldehyde derivative having a steric configuration such that in the nuclear magnetic resonance spectrum, the aldehyde proton appeared at 9.7 (in $CDCl_3$) as doublet signal (J=2 cps).

EXAMPLE 4

A mixed solution of 0.5 g of 9-carboxy-2-trans-nonenal, 1 g of cyclopentadiene and 3 ml of xylene was heated in an autoclave for 7 hours at 130°C.

An acidic substance was extracted from the reaction product. The acidic substance (free acid) obtained was converted to its methyl ester by treatment with diazomethane, and then purified by chromatography to yield about 0.1 g of bicyclo-[2.2.1]hept-5-ene-3-(6'-carbomethoxyhexyl)- 2-carboxaldehyde which corresponded to a methyl ester of the compound obtained in Example 3.

0.3 grams of ethyl 9-carboethoxy-2-trans-noneate (diethyl)-octene-1,8-dicarboxyate) and 2 g of cyclopentadiene were diluted with 15 ml of toluene, and the solution was heated in an autoclave for 7 hours at about 120°C.

The product was treated in an usual manner, and the crude oily substance obtained was subjected to chromatography on silica gel to yield 0.1 g of ethyl bicyclo[2.2.1]hept-5-ene-3-(6'-carboethoxyhexyl)-2-carboxylate which had the following characteristics.

Infrared absorption (film method): 1735, 1240, 1170.

In the nuclear magnetic resonance (in $CCl_4$): multiplet based on the olefinic protons appeared at 6.2, and multiplet based on the methyne protons appeared at 2.85 and 3.0.

There was recovered 0.5 g of unreacted starting material, the noneic acid ethyl ester.

EXAMPLE 6

Two grams of 10-carboethoxy-2-trans-decononitrile and 4 g of cyclopentadiene were diluted with 10 ml of toluene, and the solution was heated in an autoclave for 7 hours at about 120°C.

The product was treated in an usual manner. The crude oily substance obtained was subjected to chromatography on silica gel to yield 1.5 g of bicyclo[2.2.1-]hept-5-ene-3-(7'-carboethoxyheptyl)-2-carbonitrile which had the following characteristics: Infrared absorption (film method): 2230, 1740, 1240, 1170.

In the nuclear magnetic resonance (in $CCl_4$): multiplet based on the olefinic protons appeared at 6.1, and multiplet based on the methyne protons 2.9 and 3.1.

There was recovered 0.5 g of unreacted starting decanonitrile.

EXAMPLE 7

12 grams of 9-carboethoxy-2-trans-nonenonitrile and 35 g of cyclopentadiene were heated in an autoclave for 7 hours at about 150°C. The crude oily substance obtained was subjected to chromatography on silica gel to yield 6.9 g of bicyclo[2.2.1]hept-5-ene-3-endo-(6'-carboethoxyhexyl)-2-exo-carbonitrile and 1.8 g of bicyclo[2.2.1]hept-5-ene-3-exo-(6'-carboethoxyhexyl)-2-endo-carbonitrile. There was recovered 2.7 g of unreacted nonenonitrile derivative. The properties of the bicycloheptene derivatives were as follows.

2-exo-carbonitrile derivative. Infrared absorption (film method): 2250, 1735, 1245, 1180; nuclear magnetic resonance (in CCl$_4$): 6.1–6.3 (multiplet, 2H, olefnic protons), 3.1 (multiplet, H, methyne proton at the 1-position), 2.9 (multiplet, H, methyne proton at the 4-position).

2-endo-carbonitrile derivative. Infrared absorption (film method): 2250, 1735, 1245, 1180; nuclear magnetic resonance (in CCl$_4$): 6.4 (double doublet, H, olefinic proton at the 5-position), 6.2 (double doublet, H, olefinic proton at the 6-position), 3.1 (multiplet, H, methyne proton at the 1-position), 2.6 (multiplet, H, methyne proton at the 4-position).

EXAMPLE 8

0.5 grams of 9-chlorocarbonyl-2-trans-noneic acid chloride and 1 g of cyclopentadiene were diluted with 10 ml of toluene, and the diluted solution was heated in an autoclave for 5 hours at 80°C.

The reaction product was poured into an aqueous solution of sodium carbonate, and treated in an usual manner to afford about 0.4 g of an acidic substance which was found to contain bicyclo[2.2.1]hept-5-ene-3-(6'-carboxyhexyl)-2-carboxylic acid. This crude acidic substance was treated with diazomethane to convert it to its methyl ester, and then subjected to chromatography on silica gel to yield methyl bicyclo[2.2.1]hept-5-ene-3-(6'-carbomethoxyhexyl)-2-carboxylate having the following characteristics: Infrared absorption (film method): 1735, 1240, 1170. In the nuclear magnetic resonance spectrum (in CCl$_4$): multiplet appeared at about 6.2 based on the olefinic protons.

EXAMPLE 9

10.9 grams of 5-chloro-2-trans-pentenonitrile and 83 g of cyclopentadiene were heated in an autoclave for 4 hours at about 155°C. The crude oily substance obtained was submitted to chromatography on silica gel to yield 9.6 g of bicyclo[2.2.1]hept-5-ene-3-endo-(2'-chloroethyl)-2-exo-carbonitrile and 3.2 g of bicyclo[2.2.1]hept-5-ene-3-exo-(2'-chloroethyl)-2-endo-carbonitrile. The properties of these compounds were as follows.

2-exo-carbonitrile derivative. Infrared absorption (film method): 3080, 2250, 1450, 1435, 1340, 1280; nuclear magnetic resonance (in CCl$_4$): 6.15 (multiplet, 2H, olefinic protons), 3.15 (multiplet, H, methyne proton at the 1-position), 3.0 (multiplet, H, methyne proton at the 4-position), 3.55 (triplet like, 2H, methylene protons adjacent to chlorine).

2-endo-carbonitrile derivative. Infrared absorption (film method): 3080, 2250, 1450, 1435, 1340, 1280; nuclear magnetic resonance (in CCl$_4$): 6.45 (double doublet, H, olefinic proton at the 5-position), 6.2 (double doublet, H, olefinic proton at the 6-position), 3.15 (multiplet, H, methyne proton at the 1-position), 2.7 (multiplet, H, methyne proton at the 4-position), 3.6 (triplet, 2H, methylene protons adjacent to chlorine).

EXAMPLE 10

1.4 grams of methyl 5-chloro-2-trans-pentenoate and 5.0 g of cyclopentadiene were heated for 5 hours at about 145°C. The crude oily substance was subjected to chromatography on silica gel to yield 0.85 g of methyl bicyclo[2.2.1]hept-5-ene-3-endo-(2'-chloroethyl)-2-exo-carboxylate and 0.55 g of methyl bicyclo[2.2.1]hept-5-ene-3-exo-(2'-chloroethyl)-2-endo-carboxylate.

The properties of these compounds were as follows:

2-exo-carboxylate derivative. Infrared absorption (film method): 3040, 1730, 1420, 1320, 1260, 1190, 1160; nuclear magnetic resonance (in CCl$_4$): 6.15 (multiplet, 2H, olefinic protons), 3.66 (singlet, 3H, methyl ester protons), 3.50 (triplet, 2H, methylene protons adjacent to chlorine), 2.95 (multiplet, 2H, two methyne protons at the 1- and 4-position).

2-endo-carboxylate derivative. Infrared absorption (film method): 3040, 1730, 1420, 1320, 1260, 1190, 1160; nuclear magnetic resonance (in CCl$_4$): 6.25 (double doublet, H, olefinic proton at the 5-position), 6.0 (double doublet, H, olefinic proton at the 6-position), 3.60 (singlet, 3H, methyl ester protons), 3.58 (triplet, 2H, methylene protons adjacent to chlorine), 3.15 (multiplet, H, methyne proton at the 1-position), 2.60 (multiplet, H, methyne proton at the 4-position).

EXAMPLE 11

0.3 grams of 5-chloro-2-trans-pentenoic acid and 3.0 g of cyclopentadiene were heated for 5 hours at 140°C. Acidic materials were isolated in an usual manner to yield 0.3 g of an isomeric mixture of bicyclo[2.2.1]hept-5-ene-3-(2'-chloroethyl)-2-carboxylic acid. Infrared absorption (film method): 3200–2600, 1730, 1420, 1330, 1320, 1290, 1270, 1260.

EXAMPLE 12

0.2 grams of 5-hydroxy-2-trans-pentenonitrile and 2.0 g of cyclopentadiene were heated for 5 hours at about 150°C. Working up in a similar manner to that described in Example 9 yielded about 0.1 g of an isomeric mixture of bicyclo[2.2.1]hept-5-ene-3-(2'-hydroxyethyl)-2-carbonitrile.

EXAMPLE 13

3.1 grams of bicyclo[2.2.1]hept-5-ene-3-endo-(6'-carboethoxyhexyl)-2-exo-carbonitrile was dissolved in 50 ml of methylene chloride, and ozone gas was passed through the solution at −40°C until the starting compound was completely consumed.

The reaction mixture containing the ozonide was added dropwise to a mixed solution of 18 ml of formic acid and 18 ml of a 30% aqueous solution of hydrogen peroxide heated to 40°C, and the methylene chloride was removed simultaneously by distillation. The reaction mixture was further heated for 30 minutes at 60°–70°C with stirring. After addition of 100 ml of ethyl acetate to the reaction mixture, an acidic substance was extracted with an aqueous solution of sodium bicarbonate, and then treated in an usual manner to yield 3.1 g of 2-(6'-carboethoxyhexyl)-3,5-dicarboxy-cyclopentane-carbonitrile as an oily substance.

The configuration of the product was that the carboxyl groups at the 3- and 5-position and the carboethoxyhexyl groups at the 2-position are all cis to each other, and the carbonitrile groups at the 1-position is trans thereto.

The product obtained had the following characteristics. Infrared absorption (film method): 3200–2650, 2250, 1735, 1710, 1180. The product was then treated with diazomethane to convert it to a 3,5-dicarbomethoxy derivative which had the following characteristics. Infrared absorption (film method): 1735, 2250, 1260, 1170; nuclear magnetic resonance (in $CCl_4$): 4.08 (2H, quartet signal), the methyl ester signal at the 3- and 5-position appeared as singlet signal at 3.7 and 3.8; the methyne proton at the 3- and 5-position appeared as multiplet at about 3.0.

EXAMPLE 14

1.7 grams of bicyclo[2.2.1]hept-5-ene-3-endo-(6'-carboethoxyhexyl)-2-exo-carbonitrile was dissolved in 40 ml of ethanol, and ozone gas was passed through the solution at −40°C. Ethanol (90 ml) was additionally supplied at −10°C. 1.5 g of sodium borohydride was added and the solution was stirred for 30 minutes. Thereafter, the solution was further stirred for 30 minutes at room temperature. Acetone was added to consume excess sodium borohydride. The solvent was removed by distillation, and 30 ml of an aqueous solution of ammonium chloride was added to decompose the resulting complex compound. The resulting oil phase was extracted with ethyl acetate from the aqueous layer, and treated in an usual manner to yield 1.6 g of 2-(6'-carboethoxyhexyl)-3,5-bis-hydroxymethyl-cyclopentanecarbonitrile as an oily substance which had the following characteristics: Infrared absorption (film method): 2250, 1735, 1250, 1180; nuclear magnetic resonance (in $CCl_4$): the carbinol methylene proton signal at the 3- and 5-position appeared at about 3.8.

EXAMPLE 15

In the same manner as set forth in Example 13, 0.55 g of a mixture of methyl bicyclo[2.2.1]hept-5-ene-3-endo-(6'-carboethoxyhexyl)-2-exo-carboxylate and methyl bicyclo[2.2.1]hept-5-ene-3-exo-(6'-carboethoxyhexyl)-2-endo-carboxylate (the former being contained in a larger amount) was reacted, and after-treated. There was obtained 0.4 g of methyl 2-(6'-carboethoxyhexyl)-3,5-dicarboxy-cyclo-pentanecarboxylate as an oily substance. This substance was treated with diazomethane, and purified as a tricarbomethoxy derivative to yield 0.41 g of a colorless oily substance which has the following characteristics. Infrared absorption (film method): 2250, 1735, 1250, 1180; nuclear magnetic resonance (in $CCl_4$): there was hardly any difference in chemical shift among the methyl proton signals of the three methyl esters, and the signals appeared at about 3.6.

EXAMPLE 16

In the same manner as set forth in Example 13, 0.46 g of bicyclo[2.2.1]hept-5-ene-3-endo-(2'-chloroethyl)-2-exo-carbonitrile was reacted, and after-treated. There was obtained 0.35 g of 2-(2'-chloroethyl)-3,5-dicarboxycyclopentane-carbonitrile. The configuration of the product is that the carboxyl groups at the 3- and 5-position and the chloroethyl group at the 2-position are all cis to each other, and the carbonitrile group at the 1-position is trans thereto.

The product obtained has the following characteristics: Infrared absorption (film method): 3200–2500, 2270, 1715, 1215, 1050, 1030, 1000; nuclear magnetic resonance (in $Co(CD_3)_2$): 3.73 (triplet, 2H, methylene protons adjacent to chlorine), 2.5–3.3 (overlapping signals for three methyne protons at the 1-, 3- and 5-position).

EXAMPLE 17

In the same manner as set forth in Example 13, 0.68 g of methyl bicyclo[2.2.1]hept-5-ene-3-endo-(2'λ chloroethyl)-2-exo-carboxylate was reacted, and after-treated.

There was obtained 0.4 g of methyl 2-(2'-chloroethyl)-3,5-dicarboxy-cyclopentane-carboxylate. The configuration of the product is that the carboxyl groups at the 3- and 5-position and the chloroethyl group at the 2-position are all cis to each other, and the carbomethoxy group at the 1-position is trans thereto.

The product obtained has the following characteristics. Infrared absorption (film method): 3500–2600, 1730–1710, 1440, 1375, 1260, 1180; nuclear magnetic resonance (in $CDCl_3$): 3.61 (triplet, 2H, methylene protons adjacent to chlorine), 3.77 (singlet, 3H, methyl ester protons).

EXAMPLE 18

In the same manner as set forth in Example 13, 0.265 g of methyl bicyclo[2.2.1]hept-5-ene-3-exo-(2'-chloroethyl)-2-endo-carboxylate was reacted, and after-treated. There was obtained 0.265 g of methyl 2-(2'-chloroethyl)-3,5-dicarboxy-cyclo-pentanecarboxylate. The configuration of the product is that the carboxyl groups at the 3- and 5-position and the carbomethoxy group at the 1-position are all cis to each other, and the chloroethyl group at the 2-position is trans thereto. The product obtained has the following characteristics.

Infrared absorption (film method): 3200–2500, 1735–1710, 1250, 1190, 1025, 1000; nuclear magnetic resonance (in $CO(CD_3)_2$): 3.63 (triplet, 2H, methylene protons adjacent to chlorine), 3.67 (singlet, 3H, methyl ester protons).

EXAMPLE 19

In the same manner as set forth in Example 13, 0.25 g of methyl bicyclo[2.2.1]hept-5-ene-3-endo-bromomethyl-2-exo-carboxylate was reacted, and after-treated. There was obtained 0.15 g of methyl 2-bromomethyl-3,5-dicarboxy-cyclopentanecarboxylate. The product obtained had the following characteristics. Infrared absorption (film method): 3500–2600, 1740–1710, 1440, 1375, 1250, 1200, 1050, 1020.

EXAMPLE 20

0.36 grams of bicyclo[2.2.1]hept-5-ene-3-endo-(2'-chloroethyl)-2-exo-carbonitrile in 2.5 ml of ethyl acetate was subjected to ozonolysis in a manner similar to that described in Example 13. The ozonide obtained was treated with an aqueous solution of sodium bisulfite at 80°C, for 0.5 hour, followed by contacting with 60% sulfuric acid at 60°C for 1 hour. Working up as an usual manner afforded 0.3 g of crude oily substance, which was purified by chromatography to yield 2-(2'-chloroethyl)-3,5-diformylcyclopentanecarbonitrile.

In its nuclear magnetic resonance spectrum aldehyde protons appeared at about 9.8.

EXAMPLE 21

In the same manner as set forth in Example 14, 1.4 g of bicyclo[2.2.1]hept-5-ene-3-(6'-carboethoxyhexyl)-2-carboxaldehyde ethylene glycol acetal was reacted, and after-treated. There was obtained 1.3 g of 2-(6'-carboethoxyhexyl)-3,5-bis-hydroxymethyl-cyclopentane-carboxaldehyde ethylene glycol acetal. The properties of this product was as follows: Infrared absorption (film method): 3425, 1735, 1460, 1370, 1180, 1040; nuclear magnetic resonance (in $CCl_4$): 3.6 (multiplet, 4H, two methylene protons adjacent to hydroxy group), about 3.85 (multiplet, 4H, two acetal methylene protons).

EXAMPLE 22

In the same manner as set forth in Example 13, 0.6 g of methyl bicyclo[2.2.1]hept-5-ene-3-endo-cyanomethyl-2-exo-carboxylate was reacted, and after-treated.

There was obtained 0.3 g of methyl 2-cyanomethyl-3,5-dicarboxy-cyclopentanecarboxylate. The properties of this oily substance were as follows. Infrared absorption (film method): 3500–2650, 2250, 1720, 1440, 1375, 1175. Nuclear magnetic resonance (in $CDCl_3$): 3.6 (singlet, 3H, methyl ester protons), 2.35 (doublet, 2H, methylene protons adjacent to cyano group).

EXAMPLE 23

Into a mixture of 0.36 g of bicyclo[2.2.1]hept-5-ene-3-endo-(2'-chloroethyl)-2-exo-carbonitrile, 26 mg of osmium tetraoxide, 6 ml of water and 6 ml of ether, was added portionwise, 0.93g of sodium metaperiodate at room temperature during 40 minutes.

The reaction mixture was stirred further for 80 minutes, and then after-treated in an usual manner. There was obtained 0.30 g of an oily material which was composed of 2-(2'-chloroethyl)-3,5-diformyl-cyclopentanecarbonitrile and unreacted bicycloheptane derivative. In its nuclear magnetic resonance spectrum, aldehyde proton signals appeared at about 9.8.

EXAMPLE 24

Two grams of 2-(6'-carboethoxyhexyl)-3,5-dicarboxy-cyclopentanecarbonitrile was dissolved in 14 ml of toluene and 1 ml of dimethylformamide, and the solution was heated to 80°–85°C. Phosgene was passed through the solution for about 1 hour. The reaction mixture was cooled, and the toluene layer was separated. Removal of the solvent yielded 2.0 g of an acid halide derivative of said cyclopentanecarbonitrile.

A solution of 2.0 g of the acid halide derivative obtained above in 10 ml of ether was added dropwise at room temperature to 200 ml of an ether solution containing diazomethane in an amount more than 4 times on a molar basis the calculated amount, and the solution was stirred for 2 hours. Ether was removed by distillation under reduced pressure to yield 20 g of 2-(6'-carboethoxyhexyl)-3,5-bis-diazoacetyl-cyclopentanecarbonitrile.

From an acid halide derivative obtained by treating 2.0 g of the starting dicarboxylic acid derivative with thionyl chloride, 0.5 g of the bis-diazoacetyl derivative was likewise obtained.

Infrared absorption (film method): 2250, 2150, 1730, 1630; two grams of 2-(6'-carboethoxyhexyl)-3,5-bis-diazoacetyl-cyclopentanecarbonitrile so obtained was dissolved in 60 ml of chloroform. The resulting solution was added to 15 ml of 48% hydroiodic acid while cooling with ice, and the mixture was stirred for 5 minutes. On addition of 20 ml of water, the chloroform layer was separated. After washing with water, 2.0 g of an oily substance was obtained, which was then purified by chromatography on silica gel to yield 1.2 g of 2-(6'-carboethoxyhexyl)-3,5-diacetyl-cyclopentanecarbonitrile which had the following characteristics. Infrared absorption (film method): 2150, 1735, 1710, 1360, 1170; nuclear magnetic resonance (in $CCl_4$): 4.07 (2H, quartet signal), the methyl proton signals of the acetyl groups at the 3- and 5-position appeared at 2.17 and 2.26. The stereochemistry of the product is that the acetyl groups at the 3- and 5-position and the side chain at the 2-position are all cis to each other, and the carbonitrile group at the 1-position is trans to them.

EXAMPLE 25

One gram of 2-(6'-carboethoxyhexyl)-3,5-dicarboxy-cyclopentanecarbonitrile was dissolved in 20 ml of anhydrous tetrahydrofuran, and with addition of 0.59 g of triethyl amine, the reaction mixture was cooled to −5°C. A solution of 0.63 g of ethyl chloroformate in 10 ml of anhydrous tetrahydrofuran was added dropwise to the cooled reaction mixture, followed by stirring for 30 minutes. The precipitate formed was separated by filtration, and the resulting solution was added dropwise to an ether solution containing excess diazomethane in the same manner as set forth in Example 24, followed by stirring overnight.

The solvent was removed by distillation to yield 0.2 g of 2-(6'-carboethoxyhexyl)-3,5-bis-diazoacetyl-cyclopentanecarbonitrile which corresponded in infrared absorption with the product of Example 24. This product was converted to 2-(6'-carboethoxyhexyl)-3,5-diacetyl-cyclopentanecarbonitrile by the procedure shown in Example 24.

EXAMPLE 26

Two grams of 2-(6'-carboethoxyhexyl)-3,5-bis-diazoacetyl-cyclopentanecarbonitrile obtained in the same manner as in Example 24 was dissolved in 20 ml of chloroform and by introducing hydrogen chloride, 1.5 g of 2-(6'-carboethoxyhexyl)-3,5-bis-chloroacetyl-cyclopentanecarbonitrile was obtained. This product was dissolved in 30 ml of acetic acid, and 7 g of zinc powder was added. While cooling the solution with ice, 0.5-N hydrochloric acid was added, and the solution was stirred for 3 hours. Zinc powder was separated by filtration, and the resulting aqueous solution was subjected to ether extraction to obtain 1.5 g of an oily substance. This substance was purified by chromatography on silica gel to yield 0.5 g of 2-(6'-carboethoxyhexyl)-3,5-diacetyl-cyclopentanecarbonitrile, which was found to correspond with the compound obtained in Example 24.

EXAMPLE 27

Four grams of ethyl 2-(6'-carboethoxyhexyl)-3,5-dicarboxy-cyclopentanecarboxylate was treated with 4 g of thionyl chloride. The resulting acid halide derivative was dissolved in 10 ml of ether, and the solution was added dropwise to an ether solution containing methyl cadmium which had been prepared by an usual manner from 2 g of methyl bromide, 480 mg of magnesium and 2.7 g of cadmium chloride. The reaction mixture was heated under reflux for 1 hour. Thereafter, on addition of 50 ml of dilute aqueous sulfuric acid, the complex was decomposed, and then the ether layer was separated.

The resulting oily substance (4 g) was purified by chromatography on silica-gel to yield about 1 g of ethyl 2-(6'-carboethoxyhexyl)-3,5-diacetylcyclopentanecarboxylate. In its nuclear magnetic resonance spectrum, the methyl proton signals of two acetyl groups appeared at about 2.16 and 2.25.

EXAMPLE 28

In a similar manner to that described in Example 24 except that benzene was used as solvent instead of toluene, 6.5 g of 2-(2'-chloroethyl)-3,5-dicarboxy-cyclopentanecarbonitrile was reacted, and after-treated. There was obtained 2.5 g of 2-(2'-chloroethyl)-3,5-diacetyl-cyclopentanecarbonitrile, which had the following characteristics: Infrared absorption (film method): 2250, 1710, 1425, 1360, 1240, 1170. Nuclear magnetic resonance (in CDCl$_3$): 3.65 (triplet, 2H, methylene protons adjacent to chlorine), 2.25 and 2.20 (two singlets, acetyl methyl protons). The stereochemistry of this compound corresponded to that of the starting dicarboxy-cyclopentane derivative explained in Example 16. That is, two acetyl groups at the 3- and 5- position and chloroethyl group at the 2-position are all cis to each other, and the carbonitrile group at the 1-position is trans to them.

EXAMPLE 29

In the same manner as set forth in Example 28, 0.5 g of methyl 2-(2'-chloroethyl)-3,5-dicarboxy-cyclopentanecarboxylate was reacted, and after-treated. There was obtained 0.2 g of methyl 2-(2'-chloroethyl)-3,5-diacetyl-cyclopentanecarboxylate, which had the following characteristics: Infrared absorption (film method): 1730, 1710, 1435, 1200, 1170. Nuclear magnetic resonance (in CCl$_4$): 3.7 (singlet, 3H, methyl ester protons), 3.6 (triplet, 2H, methylene protons adjacent to chlorine), 2.15 (two singlets, two acetyl methyl protons).

EXAMPLE 30

In the same manner as set forth in Example 28, 0.25 g of methyl 2-bromomethyl-3,5-dicarboxy-cyclopentanecarboxylate was reacted, and after-reacted. There was obtained 0.08 g of methyl 2-bromomethyl-3,5-diacetyl-cyclopentanecarboxylate. Nuclear magnetic resonance (in CCl$_4$): 3.7 (methyl ester protons), 2.2 (two singlets, two acetyl methyl protons).

EXAMPLE 31

A mixture of 75 mg of 2-(6'-carboethoxyhexyl)-3,5-diformyl-cyclopentanecarbonitrile was treated with an ethereal diazomethane (about 1.5 m mole) overnight. By an usual working up, a crude oily material was obtained, which was purified by chromatography on silica-gel to yield about 20 mg of 2-(6'-carboethoxyhexyl)-3,5-diacetyl-cyclopentane carbonitrile. The signals of the acetyl methyl protons in the nuclear magnetic resonance spectrum of the product corresponded to that described in Example 24.

EXAMPLE 32

Five hundred milligrams of 2-(6'-carboethoxyhexyl)-3,5-diacetyl-cyclopentanecarbonitrile and 600 mg of meta-chloroperbenzoic acid were dissolved in 30 ml of chloroform, and the solution was allowed to stand for 4 days at room temperature. The reaction mixture was then treated with a 5% solution of sodium iodide and then with a 10% solution of sodium thiosulfate. Five hundred (500) milligrams of the resulting oily substance was purified by chromatography on silica gel to yield 200 mg of 2-(6'-carboethoxyhexyl)-3,5-diacetoxy-cyclopentanecarbonitrile which has the following characteristics: Infrared absorption (film method): 2250, 1735, 1235, 1180; Nuclear magnetic resonance (in CDCL$_3$ solvent): the absorption of the methyne protons at the 3- and 5-position were observed at about 4.9 and about 5.2; 4.10 (2H, multiplet signal), 2.05 (6H, two singlet signals acetoxymethyl proton).

EXAMPLE 33

Three hundred and twenty milligrams of 2-(6'-carbomethoxyhexyl)-3,5-diacetyl-cyclopentanecarbonitrile was added to 15 ml of a chloroform solution of 360 ml of metachloroperbenzoic acid, and the solution was allowed to stand for 5 days at room temperature.

The reaction mixture was treated by the same procedure as set forth in Example 32 to form a crude oily substance containing 2-(6'-carbomethoxyhexyl)-3,5-diacetoxy-cyclopentanecarbonitrile. (The nuclear magnetic resonance spectrum of this compound was similar to that of the compound set forth in Example 32, but at 3.65, a singlet signal based on the methyl ester proton was observed.)

The oily product was allowed to stand overnight in a mixed solution of 2 ml of a 10% aqueous solution of sodium hydroxide and 2 ml of methanol, and saponified under cooling. After acid precipitation, an acidic substance was extracted to obtain a crude oily substance containing 2-(6'-carboxyhexyl)-3,5-dihydroxy-cyclopentanecarbonitrile. The oily substance was treated with diazomethane to convert it to its methyl ester which was purified by chromatography to yield about 80 mg of 2-(6'-carbomethoxhhexyl)-3,5-dihydroxy-cyclopentanecarbonitrile which has the following characteristics: Infrared absorption (film method): 3420, 2225, 1730, 1710, 1240, 1170, 1085, 1020; nuclear magnetic resonance (in CDCl$_3$): The carbonitrile derivative obtained above could be converted to an aldehyde derivative according to the Stephen reaction, namely, 2-(6'-carboethoxyhexyl)-3,5-diacetoxy-cyclopentanecarboxaldehyde. The properties of this aldehyde derivative were as follows: Infrared absorption (film method): 2825, 2750, 1735, 1720, 1250, 1240, 1175, 1100, 1030. Nuclear magnetic resonance (in CDCl$_3$): 9.85 (doublet, J=2 cps, aldehyde proton), 2.0 (two singlets, two acetoxy methyl protons), about 4.0 and about 4.5 (two multiplets, two carbinol methyne protons at the 3- and 5-position), 3.65 (singlet, methyl ester protons).

EXAMPLE 34

A mixture of 0.46 g of 2-(2'-chloroethyl)-3,5-diacetyl-cyclopentanecarbonitrile, 2.05 g of meta-chloroperbenzoic acid and 15 ml of chloroform was heated at 50°C for 4 days. The reaction mixture was treated by the same procedure as set forth in Example 32 to afford 0.40 g of 2-(2'-chloroethyl)-3,5-diacetoxy-cyclopentanecarbonitrile as an oily substance. The product had the following characteristics: Infrared absorption (film method): 2250, 1740, 1430, 1370, 1230, 1045, 1020. Nuclear magnetic resonance (in CDCl$_3$): about 5.3 (two multiplet, 2H, two methyne protons at the 3- and 5-position), 3.65 (triplet, J=7 cps, methylene protons adjacent to chlorine), 2.10 (two singlets, two acetoxy protons).

EXAMPLE 35

The same cyclopentane derivative as described in Example 34 was obtained by oxidation of 2-(2'-chloroethyl)-3,5-diacetyl-cyclopentanecarbonitrile with permaleic acid which had been prepared from maleic anhydride and 90% hydrogen peroxide.

What is claimed is:

1. Cyclopentane derivatives of the formula

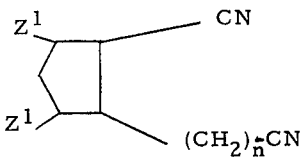

wherein $n$ is an integer of from 1 to 7 and $Z^1$ is selected from the group consisting of formyl, carboxyl, hydroxymethyl, and acetyl.

2. The cyclopentane derivatives according to claim 1, wherein $n$ is an integer of from 1 to 2.
3. The cyclopentane derivatives according to claim 1, wherein $n$ is 1.
4. The cyclopentane derivatives according to claim 1, wherein $Z^1$ is selected from the group consisting of carboxyl, formyl and hydroxymethyl.
5. The cyclopentane derivatives according to claim 1, wherein $Z^1$ is acetyl.
6. Cyclopentane derivatives of the formula

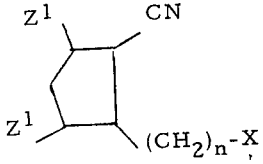

wherein X is alkoxy carbonyl, $n$ is an integer of from 1 to 7, and $Z^1$ is selected from the group consisting of formyl, carboxyl, hydroxymethyl, and acetyl.

7. The cyclopentane derivatives according to claim 6 wherein $n$ is an integer of from 1 to 2.
8. The cyclopentane derivatives according to claim 6, wherein $n$ is 1.
9. The cyclopentane derivatives according to claim 6, wherein $Z^1$ is selected from the group consisting of carboxyl, formyl and hydroxymethyl.
10. The cyclopentane derivatives according to claim 6, wherein $Z^1$ is acetyl.
11. Cyclopentane derivatives of the formula

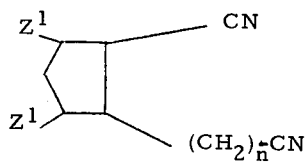

wherein $n$ is an integer of from 1 to 7 and $Z^1$ is Hal—CH$_2$CO—, wherein Hal is a halogen atom.

12. Cyclopentane derivatives of the formula

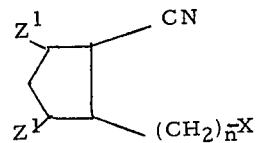

wherein X is alkoxycarbonyl, $n$ is an integer of from 1 to 7 and $Z^1$ is Hal—CH$_2$CO—, wherein Hal is a halogen atom.

13. A process for producing a cyclopentane derivative of the formula (Ia)

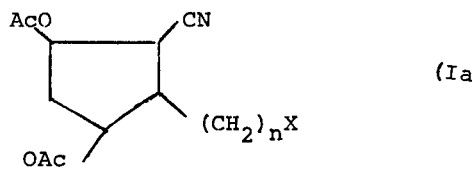

(Ia)

wherein Ac represents an acetyl group, $n$ is an integer of from 1 to 7; and X is a cyano or alkoxycarbonyl group, which comprises:

1. reacting a compound of the formula (III)

X—(CH$_2$)$_n$CH=CH—CN  (III)

wherein X and $n$ are as defined above, with cyclopentadiene at 0°–200°C to yield a bicycloheptene derivative of the formula (II)

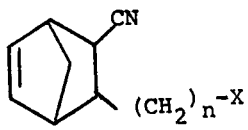

wherein X and *n* are as defined above;
2. oxidizing the bicycloheptene derivative of formula II with ozone at −78° to 100°C to yield an ozonide of the bicycloheptene derivative of formula (II), and
3. further oxidizing the ozonide of the bicycloheptene derivative of formula II with an organic acid and hydrogen peroxide or with hydrogen peroxide alone to yield a cyclopentane derivative of the formula (I*d*)

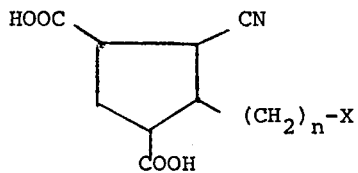

wherein X and *n* are as defined above;
4. reacting the cyclopentane derivative of formula (I*d*) with a member selected from the group consisting of thionyl chloride, phosgene and oxalic chloride to yield an acid halide of the formula (I*e*)

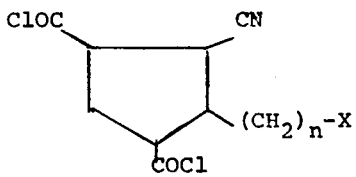

wherein X and *n* as defined above; and
5. reacting the acid halide of the formula (I*e*) with diazomethane at ambient temperature to yield a cyclopentane derivative of the formula (I*f*)

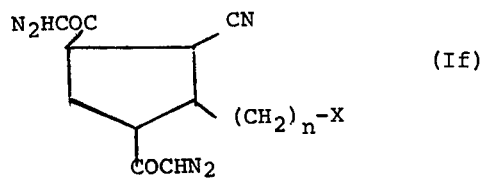

wherein X and *n* are as defined above;
6. reacting the cyclopentane derivative of formula (I*f*) with aqueous hydroiodicacid to yield a cyclopentane derivative of the formula (I*g*)

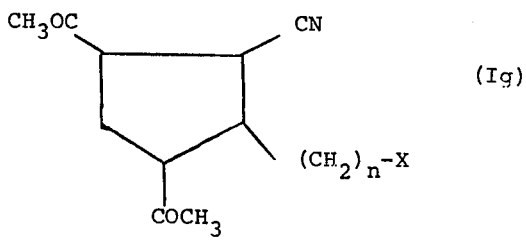

wherein X and *n* are as defined above; and
7. reacting the cyclopentane derivative of formula (I*g*) with a peracid to obtain the cyclopentane derivative of formula (I*a*).

14. The process of claim 13 wherein the peracid of step (7) is selected from the group consisting of meta-chloroperbenzoic and peracetic acid and trifluoroperacetic acid.

15. The process of claim 13 wherein the reaction of step (1) is performed using a ratio of the compound of formula (III) to cyclopentadiene of from 10:1 to 1:10.

* * * * *